United States Patent [19]

Wright et al.

[11] Patent Number: 4,559,953
[45] Date of Patent: Dec. 24, 1985

[54] APPARATUS FOR DETECTING CHANGES IN SHAPE OF A BODY

[75] Inventors: Basil M. Wright, Rickmansworth; Christopher A. R. Haire, Kenton, both of England

[73] Assignee: Pye (Electronic Products) Limited, Cambridge, England

[21] Appl. No.: 147,971

[22] Filed: May 8, 1980

[30] Foreign Application Priority Data

May 11, 1979 [GB] United Kingdom ............. 7916457

[51] Int. Cl.$^4$ .............................................. A61B 5/02
[52] U.S. Cl. .................................. 128/680; 128/715; 128/773
[58] Field of Search ............. 128/675, 680, 681, 687, 128/694, 715, 721, 748, 773, 774, 775, 777, 780, 782; 73/715; 179/151, 121 C, 110 A

[56] References Cited

U.S. PATENT DOCUMENTS

| | | | |
|---|---|---|---|
| 3,573,394 | 4/1971 | Birnbaum | 128/715 |
| 3,682,161 | 8/1972 | Alibert | 179/151 X |
| 3,853,188 | 12/1974 | Schendel | 128/782 |
| 3,958,562 | 5/1976 | Hakim et al. | 128/748 |
| 3,973,150 | 8/1976 | Tamura et al. | 179/110 A X |
| 4,012,604 | 3/1977 | Speidel | 128/680 X |
| 4,122,837 | 10/1978 | Leonard | 128/774 |
| 4,141,350 | 2/1979 | Shinoda | 128/680 |

Primary Examiner—Kyle L. Howell
Assistant Examiner—J. Hanley
Attorney, Agent, or Firm—Paul R. Miller

[57] ABSTRACT

An apparatus for detecting and measuring changes in the shape of a wall of a body includes a detector capsule adapted for attachment to the wall and pneumatically connected to a volume transducer responsive to changes in the internal volume of the apparatus produced by changes in the shape of the wall. The internal volume of the capsule is partially defined by a flexible diaphragm for engagement and complementary movement with the wall. The capsule contains a resiliently deformable material which presses the diaphragm into contact with the wall regardless of the convex or concave shape of the wall.

8 Claims, 5 Drawing Figures

APPARATUS FOR DETECTING CHANGES IN SHAPE OF A BODY

The present invention relates to apparatus for detecting changes in the shape of a wall of a body, and relates in particular to a detector capsule for engagement with the wall. The body may be human or animal or may be an inanimate body.

Body functions such as respiration in neonates, respiration and uterine contractions in women in advanced pregnancy and labour produce changes in the shape of the abdominal wall. Other body functions such as arterial pulsation produce changes in the shapes of other areas of the body wall.

For medical purposes, the detection of such changes of shape provides a means of detecting and measuring the corresponding body functions without undue interference with a neonate infant or a patient when under examination.

Apparatus for detecting changes in the shape of a body wall is known comprising a detector capsule adapted for attachment to the body wall and partly defined by a flexible diaphragm for engagement and complementary movement with the wall when attached thereto, the capsule being pneumatically connected to a transducer which is responsive to variations in the volume of the capsule due to changes in the shape of the wall.

Apparatus of this type for detecting abdominal expansion and contraction is described in German Offenlegungsschrift 2821223 in the name of National Research Development Corporation.

In the known apparatus, the detector capsule comprises a rigid cup-shaped body having the diaphragm located across its mouth.

A disadvantage of the known detector capsule is that it is found to operate satisfactorily when attached to a wall of convex configuration but not when attached to a wall of concave configuration.

A further disadvantage is that it is relatively complicated and expensive to manufacture. At least for medical purposes it is desirable that a detector capsule should be sufficiently cheap so as to permit it being discarded after only one use.

It is an object of the present invention to provide a detector capsule effective to detect changes in the shape of a body wall of either convex or concave curvature.

According to the present invention, a detector capsule adapted for attachment to a wall of a body and partially defined by a flexible diaphragm for engagement and complementary movement with the wall when attached thereto, the capsule being pneumatically connected to a transducer responsive to variations in the volume of the capsule due to changes in the shape of the wall is characterised by a body of resiliently deformable material located within the capsule and effective to urge the diaphragm into engagement with the wall.

The body of resiliently deformable material may be a block of flexible, open cell plastics material, for example foamed polyurethane or foamed PVC.

In one arrangement the detector capsule comprises a rigid cup-shaped body having the diaphragm located across its mouth and the body of resiliently deformable material located within the cup, the thickness of the body when in an undeformed state exceeding the depth of the cup.

In an alternative arrangement the detector capsule comprises a first flexible diaphragm for engagement with the wall, a second flexible diaphragm co-extensive with the first diaphragm and sealingly connected therewith around a peripheral region thereof, the body of resiliently deformable material being located between the first diaphragm and the second diaphragm, the capsule in use being attached to the wall by a band of substantially inextensible material passing over the second diaphragm. This arrangement provides a capsule which is more simple and less expensive to manufacture than the previously-known capsule.

In order that the invention and the manner in which it is to be performed may more readily be understood, embodiments thereof will now be described, by way of examples, with reference to the accompanying drawings, of which:

Figure 1:
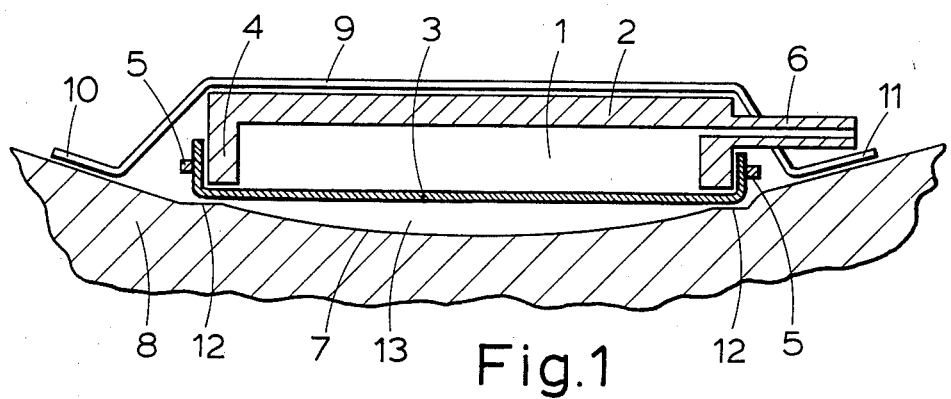
FIG. 1 is a sectional view of a known detector capsule.

Referring first to FIG. 1, a known capsule 1 comprises a rigid body 2 of simple cupped shape which is closed by a flexible diaphragm 3. The body 2 may be made of metal or any suitably rigid plastics material, and preferably comprises a circular disc hollowed on one side to leave an upstanding peripheral rim 4. For medical use, the body 2 suitably has a diameter in the range 20–30 mm, the smaller diameter being preferred for neonates and the larger for adults and the rim 4 a height of the order of 3 mm.

The diaphragm 3 may be a sheet of soft rubber secured to the rim of the body 2, for example by a retaining ring 5.

A nozzle 6 projects from the rim 6 to receive an end of a flexible tube, not shown in the drawing, employed to connect the interior of the capsule 1 to a volume transducer.

In use, the capsule 1 is attached to a wall 7 of a body 8 with the diaphragm 3 adjacent the wall. The attachment may be by means of strips of adhesive tape such as that indicated by the reference 9 which span the back of the capsule and have ends 10, 11 adhered to the wall 7 outside the periphery of the capsule.

It will be appreciated that if the wall 7 were convex, the diaphragm 3 would, when the capsule were first applied, flex in conformity with the curvature of the wall and would make contact over substantially the whole of its area. Any subsequent changes in the shape of the wall would then produce complementary changes in the shape of the diaphragm and corresponding changes in the internal volume of the capsule 1 which would be detected by the volume transducer. In the case of a concave wall 7, as shown in FIG. 1, the diaphragm 3 contacts the wall only in a peripheral region 12, leaving a void 13 between the central area of the diaphragm and the wall. In this case, the diaphragm 3 will not accurately follow changes in the shape of the wall. Both the sensitivity and the accuracy of the apparatus will be substantially reduced.

Figure 2:
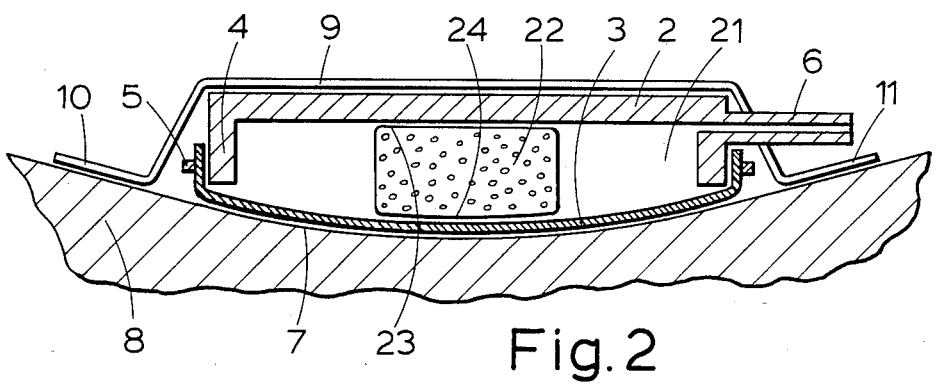
FIG. 2 is a sectional view of a first embodiment of the invention.

A first embodiment of the present invention will now be described with reference to FIG. 2, in which integers already described are accorded the same reference numerals as in FIG. 1.

The capsule 21 comprises a rigid body 2, with rim 4 and nozzle 6, and a diaphragm 3 secured by a retaining ring 5, all as hereinbefore described.

Within the capsule 21 is located a block 22 of resiliently deformable material such as a flexible, open-cell plastics foam, typically polyurethane or PVC foam, with opposed faces 23 and 24 engaging respectively the inner face of the body 2 and the inner face of the diaphragm 3. The distance between the faces 23 and 24, when the block 22 is in its undeformed state is greater than the height of the rim 4. Consequently the diaphragm 3 is initially bowed outward.

When the capsule 21 is secured to a concave wall 7 of a body 8, e.g. by adhesive tapes 9, the block 22 deforms as necessary to maintain the diaphragm in contact with the wall over substantially the whole of its area, both initially and during subsequent changes in the shape of the wall. It may be noted that the capsule 21 is equally effective when secured to a convex wall, the block 22 merely being deformed to a somewhat greater extent than in the case of a concave wall. In effect, the block 22 serves as a spring effective to maintain the diaphragm 3 in contact with the wall 7 regardless of whether the wall is convex or concave.

The embodiment described with reference to FIG. 2 thus satisfies the first object of the invention, but it remains relatively expensive to manufacture.

Figure 4:
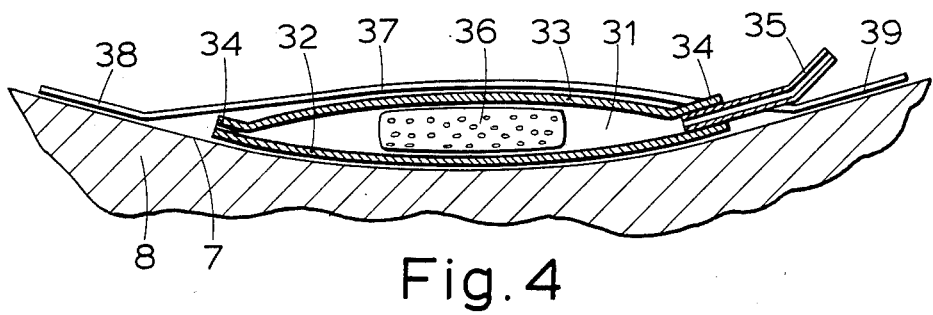
FIG. 4 is a sectional view of the embodiment of FIG. 3 applied to a concave wall.
Figure 3:
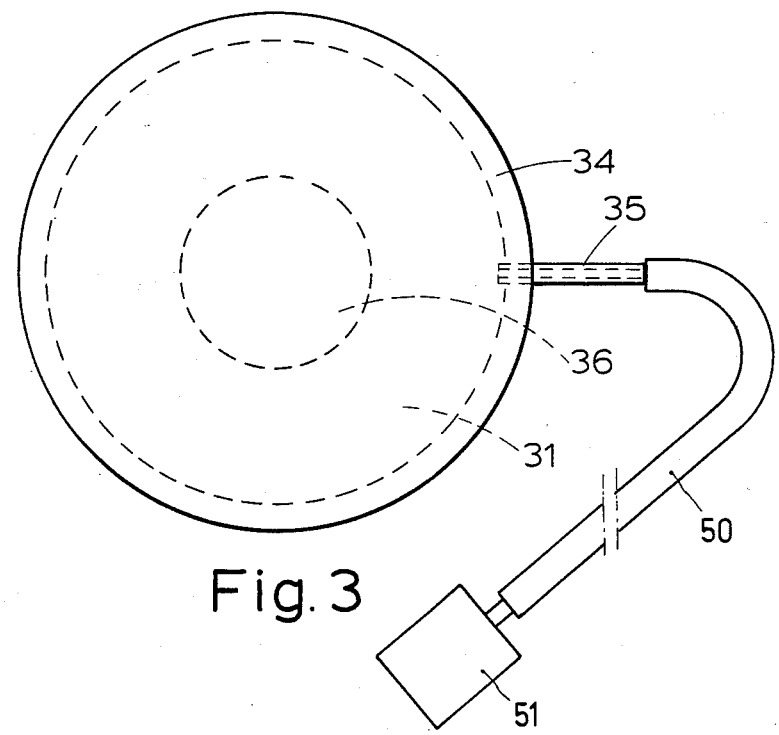
FIG. 3 is a plan view of a second embodiment of the invention.
Figure 5:
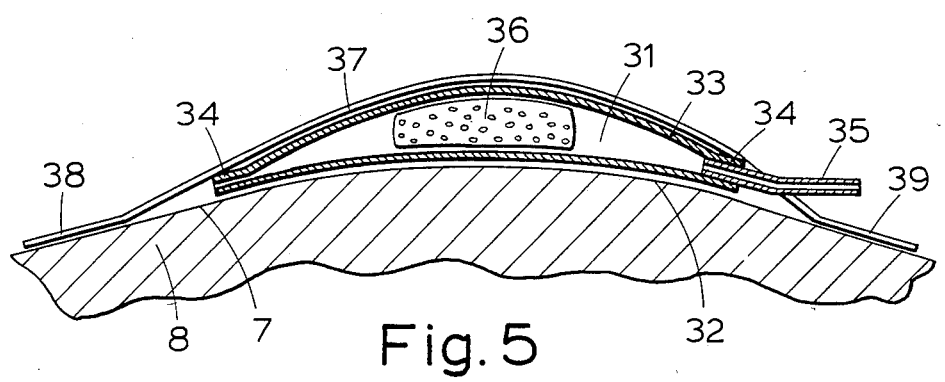
FIG. 5 is a sectional view of the embodiment of FIG. 3 applied to a convex wall.

A second embodiment of the invention, more suitable for manufacture in quantity at low cost, will now be described with reference to FIGS. 3, 4 and 5, in which corresponding integers are accorded identical reference numbers.

A capsule 31 comprises a first flexible diaphragm 32 and a second flexible diaphragm 33 coextensive with the first diaphragm and sealingly connected therewith in a peripheral area 34. The diaphragms 32 and 33 preferably comprise respective circular discs of e.g. PVC sheet 0.12 mm thick and 20 to 30 mm diameter, joined around their edges by r.f. welding. An end of a PVC tube 35 is secured in the joint 34, e.g. by welding or by use of a suitable adhesive so that the bore of the tube communicates with the interior of the capsule 31. The tube 35 is connectible to a volume transducer not shown in the drawings.

A block 36 of resiliently deformable material such as polyurethane foam or PVC foam typically 3 mm thick is centrally disposed between the diaphragms 32 and 33.

In use, the capsule 31 is attached to a wall 7 of a body 8, with the diaphragm 32 adjacent the wall, for example by strips of adhesive tape such as that indicated by the reference 37 spanning the capsule and having ends 38, 39 adhered to the body 8 outside the periphery of the capsule. Attachment to a concave wall is illustrated in FIG. 4 and attachment to a convex wall in FIG. 5. It will be seen that consequent on the flexibility of the diaphragms 32 and 33 and of the block 36, the capsule 31 can readily conform to the shape of the wall 7, whether it be concave or convex.

In operation, the length of the tape 37 remains substantially constant. Therefore, if the wall 7 expands (due for example, to the patient breathing in) the effect is to tension the tape across the back of the capsule 31 and at the same time to push the diaphragm 32 towards the diaphragm 33, the block 36 deforming to accommodate this motion, and so to reduce the internal volume of the capsule. If the wall 7 subsequently contracts, due for example to exhalation the block 36 returns to its former shape, maintaining the diaphragm 32 in contact with the wall and so increasing the internal volume of the capsule.

It will be appreciated that the capsule 31 may equally be applied so that diaphragm 33 is adjacent the wall 7 and the tape 37 is in contact with the diaphragm 32.

In an alternative arrangement, a flexible but inextensible band which encircles both the capsule 31 and the body 8 may be employed instead of the adhesive tape strips for securing the capsule to the wall 7.

Detector capsules according to the present invention are not restricted to the circular configuration hereinbefore described but may be of any convenient configuration in plan form.

Although described herein with particular reference to medical use, detector capsules according to the invention are not restricted to such uses, but may equally be employed for veterinary purposes and for detecting changes in the shapes of inanimate bodies.

We claim:

1. A detector capsule for being attached to a wall of a body, said capsule comprising at least one flexible diaphragm, one said flexible diaphragm engaging and moving complementarily with both concave and convex distensions of said wall, means for pneumatically connecting said capsule to a transducer responsive to variations in volume in said capsule as a result of changes in said wall, and means including resiliently deformable material located within said capsule for constantly urging said one diaphragm into virtually complete engagement with said wall.

2. A detector capsule according to claim 1, wherein said means including resiliently deformable material is a block of a flexible, open-cell plastics foam.

3. A detector capsule according to claim 2, wherein said block of plastics foam is polyurethane foam.

4. A detector capsule according to claim 2, wherein said block of plastics foam is PVC foam.

5. A detector capsule according to claim 1, wherein said capsule includes a rigid cup-shaped structure having said one diaphragm located across the open end, and said resiliently deformable material is internally located in said structure, and wherein said resiliently deformable material has a thickness exceeding the depth of said cup-shaped structure when in an undeformed state.

6. A detector capsule according to claim 1, wherein said capsule includes two flexible diaphragms comprising said one diaphragm engaging said wall and a second said diaphragm being coextensive with said one diaphragm and sealingly connected around the periphery thereof, said resiliently deformable material being located internally between said one diaphragm and said second diaphragm, and wherein said capsule is attached to said wall by a band of substantially inextensible material passing at least over said second diaphragm.

7. A detector capsule according to claim 6, wherein said band is an adhesive tape adhering to said wall outside the periphery of said capsule.

8. A detector capsule according to claim 6 or claim 7, wherein said band encircles both said capsule and said body.

* * * * *